United States Patent
Garonzik

(10) Patent No.: US 6,187,041 B1
(45) Date of Patent: Feb. 13, 2001

(54) OCULAR REPLACEMENT APPARATUS AND METHOD OF COUPLING A PROSTHESIS TO AN IMPLANT

(76) Inventor: Scott N. Garonzik, 6592 Patio La., Boca Raton, FL (US) 33433

( * ) Notice: Under 35 U.S.C. 154(b), the term of this patent shall be extended for 0 days.

(21) Appl. No.: 09/224,446

(22) Filed: Dec. 31, 1998

(51) Int. Cl.$^7$ .................. A61F 2/14; A61F 2/16
(52) U.S. Cl. .......................... 623/4.1; 623/6.64
(58) Field of Search .................. 623/4, 11, 15, 623/4.1, 6.64

(56) References Cited

U.S. PATENT DOCUMENTS

| | | | | |
|---|---|---|---|---|
| 2,637,043 | * | 5/1953 | Morrell | 623/4 |
| 2,660,732 | * | 12/1953 | Stone, Jr. | 623/4 |
| 2,688,139 | * | 9/1954 | Jardon | 623/4 |
| 4,955,909 | * | 9/1990 | Ersek et al. | 623/11 X |
| 4,976,731 | * | 12/1990 | Perry | 623/4 |
| 5,026,392 | * | 6/1991 | Gordon | 623/4 |
| 5,192,315 | * | 3/1993 | Jacob-LaBarre | 623/4 |
| 5,326,346 | * | 7/1994 | Cortes | 623/4 |
| 5,713,955 | * | 2/1998 | Durette | 623/4 |
| 5,741,336 | * | 4/1998 | Fraser | 623/15 |

* cited by examiner

Primary Examiner—Michael J. Milano
Assistant Examiner—Hieu Phan
(74) Attorney, Agent, or Firm—Robert M. Downey, P.A.

(57) ABSTRACT

An ocular replacement system provides a ball-shaped implant body having an outer spherical and porous surface that is receptive to ingrowth of ocular tissue and including an anterior portion positioned forwardly when the implant is fitted in the eye cavity to create a convex tissue surface area when covered by conjunctiva. A prosthesis includes an outer face and an opposite inner concave surface shaped to conform generally to the convex tissue surface area. When fitted in the front orbital space of the eye cavity, a magnetic attractive force between at least one magnet on the inner surface of the prosthesis and one or more magnetically attractive elements on the anterior portion of the implant couples the prosthesis to the implant so that the prosthesis follows movement of the implant to simulate natural eye movement within the eye cavity. The magnets are offset relative to the attractive elements to avoid direct alignment and excessive magnetic attraction, thereby reducing pressure which may cause tissue breakdown, infection, tissue dehiscence or implant extrusion.

10 Claims, 1 Drawing Sheet

US 6,187,041 B1

OCULAR REPLACEMENT APPARATUS AND METHOD OF COUPLING A PROSTHESIS TO AN IMPLANT

BACKGROUND OF THE INVENTION

1. Field of the Invention

This invention relates generally to a prosthetic eye, and, more particularly to an improved ocular replacement apparatus that provides for integrated coupling of a prosthesis to an implant using magnetic attraction.

2. Description of the Related Art

There are instances where an eye has become damaged due to trauma or disease wherein it is necessary to remove the entire eyeball from the eye cavity. Thereafter, a prosthetic eye may be replaced in the eye cavity: to provide a cosmetically acceptable appearance; to reduce the psychological trauma associated with loss of an eye; and/or to correct any medical problems associated with the loss of an eye.

Presently, the most accepted medical procedures for the removal of a diseased natural eye is to perform either an enucleation or an evisceration. Generally, enucleation involves first sedating the patient and anesthetizing the eye. The attaching ocular muscles and tissues are then dissected completely away from the patient's diseased natural eyeball. The conjunctiva and Tenon's capsule are incised down to the sclera as close as possible to the cornea. The extra ocular muscles are disinserted at the point of their insertion on the sclera. The optic nerve is severed and the natural eyeball is removed. While controlling bleeding, a porous plastic or coral ball-shaped implant is inserted into the eye cavity. Thereafter, the ocular muscles are sutured to the exterior, porous surface of the implant, or a homologous or autologous material wrap, in accordance with their correct anatomical positions. Once muscle attachment is completed, the Tenon's capsule and conjunctiva are closed up over the implant.

There are some instances where it is desirous to perform an evisceration rather than an enucleation of the eye. Evisceration can be performed for treatment of a blind painful eye if a rapid, less traumatic surgery, as compared to enucleation. In particular, evisceration may be desirable for old or very ill patients in whom general anesthesia is a risk. Generally, evisceration involves undermining the conjunctiva with scissors that the sclera around the limbus is free of conjunctiva. A keratome entry through the limbus into the anterior chamber of the eye is performed and curved corneal scissors is used to excise the entire cornea. An evisceration spoon is used to remove the intraocular contents while the globe is fixed by holding onto the limbal sclera with toothed forceps. Thereafter, the scleral shell is opened with forceps and the uveal tissue is scraped from inside the eye using a gauze square held in a hemostat. Bleeding is controlled by cautery. The implant can then be inserted within the cavity and, thereafter, the scleral shell is closed. The ocular muscles remain in tact and, in most cases, the patient has full mobility of the ocular globe.

In either an enucleation or an evisceration, the patient is measured for a cosmetic prosthesis after a healing period of approximately two months. After another four to six months, the prosthesis is integrated with the implant. At present, the most common method to fully integrate the prosthesis with the implant involves the use of a coupling post. To fit the post to the implant, the conjunctiva is incised and pulled partially apart to expose an anterior portion of the implant. A hole is then drilled approximately 5–7 mm deep into the implant, perpendicular to the anterior surface. The coupling post is then inserted and anchored within the hole so that an exposed end portion of the post protrudes approximately 2 mm beyond the conjunctiva. The conjunctiva is then pulled closed around the base of the post over the anterior surface of the implant. A hole or other means on the inner surface of the prosthesis receives the protruding end of the post so that the prosthesis remains attached to the post. Hence, as the muscles of the eye move the implant, the coupling post serves to move the prosthesis with the implant to simulate natural eye movement.

While the above-described procedure is the most effective method presently known to couple a prosthesis to an eye implant, patients have experienced numerous problems with this technique. Specifically, fully integrated prosthetic implant devices have been disappointing in the past because of associated complications, such as extrusion of the implant and conjunctival erosion. In some instances, movement of the prosthesis and coupling post relative to the conjunctiva has caused extreme irritation to the conjunctiva tissue, resulting in infection and rejection of the implant.

In the past, others have proposed use of magnets to achieve coupling of the prosthesis to the implant. Examples of this can be found in the U.S. patents to Rosen, et al., U.S. Pat. No. 2,661,480 and Morrell, U.S. Pat. No. 2,637,043, as well as the Soviet Union patent to Riga, U.S. Pat. No. 633,525. One of the major problems encountered with these coupling systems, as well as similar magnetic coupling arrangements proposed in the past, is excessive pressure between the prosthesis and implant due to the magnets being disposed in direct axial alignment. It has been discovered that too much pressure on the eye tissue may cause tissue breakdown, which eventually may lead to infection, tissue dehiscence, or implant extrusion. These past attempts using implants with magnets disposed in direct axial alignment have never been successful. This is due largely to the fact that the excessive attraction resulting from the direct axial alignment of the magnets causes too much pressure on the conjunctiva.

There is a further problem encountered when magnets are used in the implant. In particular, it has been found that magnets, when embedded within the human body, loose their attracting abilities within approximately one year. This has been particularly proven in the use of magnets in dental implants, which are covered by mucosa tissue in the mouth, similar to the tissue found in the eye socket. Once the magnets loose their magnetically attractive characteristics, it is necessary to remove the implant to replace the magnets. This is especially a problem with orbital implants. Because the muscles and tissue become attached to the implant, major invasive surgical procedures are necessary to remove and replace the implant in the eye cavity. Once the orbital implant has become connected to the muscles, and the tissue has attached to the surface of the implant, major surgery is required to remove the implant from the eye cavity. Accordingly, it has been discovered that the use of magnets in the orbital implant is not desirable due to their limited useful life.

Accordingly, there is an urgent need in the art for an improved ocular replacement system and method to more effectively couple a prosthesis to an eye implant in a manner which reduces the likelihood of irritation, infection and/or rejection of the implant and which avoids the need for subsequent surgical invasive procedures.

SUMMARY OF THE INVENTION

The present provides an ocular replacement system including a ball-shaped implant body which is sized and configured for receipt within the eye cavity so that an anterior portion of the implant body is positioned forwardly within the eye cavity and against the conjunctiva tissue covering the implant body. The ocular replacement system further includes a prosthesis having an inner concave surface shaped to conform generally to the rounded bulge of the conjunctiva which covers the anterior portion of the implant.

In accordance with the system and method of the present invention, an improved means of coupling the prosthesis to the implant is provided, and includes one or more magnets fitted to the inner facing side of the prosthesis and one or more corresponding magnetically attractive elements embedded within the anterior portion of the implant so that a face of the attractive elements is flush with the exterior surface of the implant. The magnets are positioned on the prosthesis in a manner which avoids direct alignment with the one or more magnetically attractive elements on the implant; yet the magnets are positioned in close enough proximity to the one or more magnetically attractive elements so as to maintain a magnetic attraction between the magnets and the attractive elements. The magnetic coupling of the prosthesis to the implant causes the prosthesis to move with the implant to simulate natural eye movement without irritating and/or damaging the ocular tissue. In particular, the offset positioning of the magnets relative to the attractive elements avoids an excessive force of magnetic attraction between the prosthesis and implant which may cause tissue irritation, and possibly tissue damage, infection, dehiscence or implant extrusion.

Accordingly, it is an object of the present invention to provide an improved ocular replacement system and method of coupling a prosthesis to an implant.

More specifically, it is an object of the present invention to provide an ocular replacement system having an improved means for integrated coupling of a prosthesis to an eye implant without damaging and/or irritating the ocular tissue.

It is yet a further object of the present invention to provide an ocular replacement system which eliminates the need for a coupling post, thereby avoiding tissue irritation and damage, as well as the need for follow-up surgery after implant surgery.

It is a further object of the present invention to provide an improved ocular replacement system and method of coupling a prosthesis to an implant which significantly reduces the likelihood of tissue irritation, infection, tissue dehiscence and implant extrusion.

These and other objects and advantages of the present invention will be more readily apparent with reference to the following detailed description and the accompanying drawings.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENT

Figure 1:
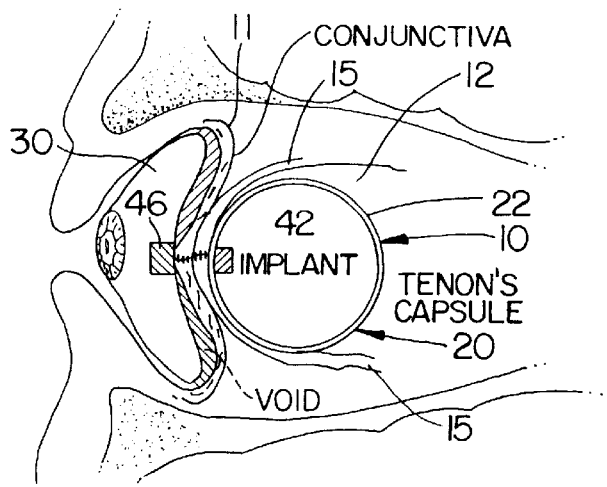
FIG. 1 is a side sectional anatomical view of the patient's eye, illustrating the eye implant and prosthesis of the replacement system of the present invention operatively received within the orbit.
Figure 3:
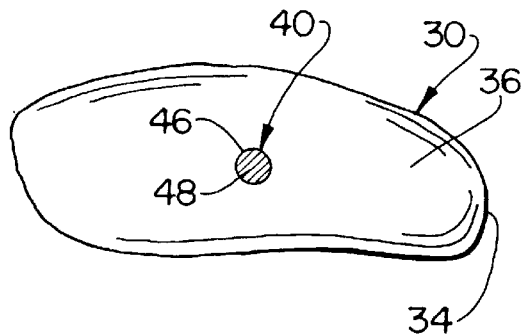
FIG. 3 is a rear elevational view of the prothesis showing a magnet embedded within the concave surface thereof to facilitate magnetic coupling with one or more magnetically attractive elements fitted to the implant.

Referring to FIG. 1, the ocular replacement apparatus 10 of the present invention is shown in accordance with an exemplary embodiment. The ocular replacement apparatus includes a generally ball-shaped implant body 20 which is sized and configured for receipt within the eye cavity 12 so that Tenon's capsule 15 surrounds the implant body 20. The implant body 20 includes a generally spherical outer surface 22, which, in a preferred embodiment, is receptive to ingrowth of ocular tissue, including muscle tissue, so that the implant body 20 integrates with the tissue of the orbit. A coral implant body or a plastic implant ball having a porous exterior surface are examples of a suitable material for promoting tissue attachment. The outer surface 22 includes an anterior portion 24 which is positioned forwardly in the eye cavity and covered by the conjunctiva 11. Due to the spherical shape of the implant, the anterior portion exerts outward pressure to impart a bulging, rounded outer configuration to the conjunctiva 11.

The apparatus 18 further includes a prosthesis 30 formed of ceramic, glass, plastic or other suitable material. The prosthesis 30 includes an outer convex surface 32 which is provided with a cosmetically acceptable appearance to resemble the natural eye. The prosthesis 30 further includes a surrounding peripheral edge 34 which is shaped and configured to generally conform with the periphery of the conjunctiva. The peripheral edge 34 is generally rounded to provide a smooth surface, thereby preventing excessive irritation of the ocular tissue upon movement of the prosthesis. An inner concave surface 36 of the prosthesis is shaped to conform to the generally rounded outer configuration of the conjunctiva.

Magnetic coupling means 40 provide an attractive force between the anterior portion 24 of the implant body 20 and the inner concave surface 36 of the prosthesis 30 to magnetically couple the prosthesis to the implant body. In this manner, the prosthesis follows movement of the implant body within the eye cavity without the need of structure extending through the conjunctiva to connect the implant body to the prosthesis.

Figure 2:
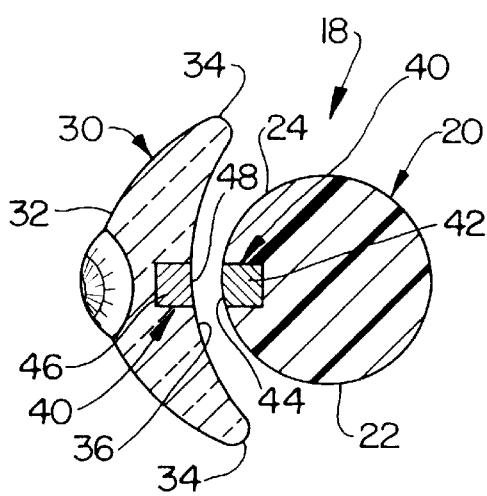
FIG. 2 is a sectional view of the implant and prosthesis of the present invention, in accordance with a preferred embodiment thereof.

In one exemplary embodiment, as seen in FIG. 2, the magnetic coupling means includes a magnetically attractive element 42 embedded with the anterior portion 24 of the implant body so that an exposed face 44 of the magnet 42 is flush with the outer surface 22. In a preferred embodiment, the attractive element 42 is formed of stainless steel or another metal alloy that is attracted to magnetic force. It is also important that the human body be receptive of the element 42 for long term implantation. A magnet 46 is embedded within the concave surface of the prosthesis so that an exposed face 48 of the magnet 46 is flush with the concave surface 36. The magnet 46 is specifically positioned on the inner concave surface 36 of the prosthesis so that the magnet face 48 is offset relative to the face 44 of the attractive element 42. This offset position maintains magnetic attraction between one or more magnets 46 and one or more attractive elements 42 while avoiding direct alignment which may cause excessive attractive force and tissue damage. Locating the second magnet 46 position on an inner concave surface 36 may be done during fitting of the prosthesis to the patient. Upon aligning the artificial eye on the outer surface 32 of the prosthesis with the gaze position of the patient's natural eye, the magnet 46 position on the prosthesis is marked. A bore or cavity is drilled in the concave surface, at the marked position, and the magnet 46 is set into place with the use of an adhesive, so that the exposed face 48 is flush with the concave surface. Instrumentation may be necessary to identify the specific location of the magnetically attractive element 42 behind the conjunctiva.

Figure 4:
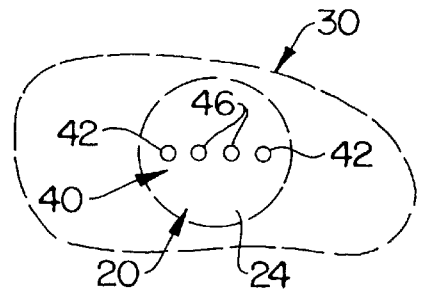
FIG. 4 is a diagrammatic view illustrating an arrangement of magnets on the prosthesis and corresponding magnetically attractive elements on the anterior portion of the implant, showing the offset positioning of the magnets relative to the attractive elements.
Figure 5:
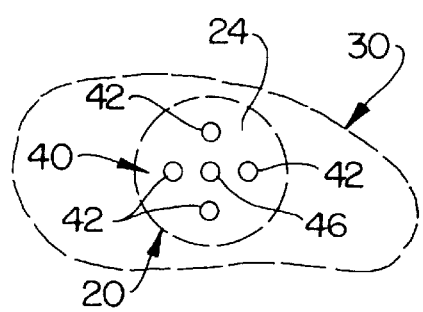
FIG. 5 is a diagrammatic view illustrating an arrangement of the magnetically attractive elements on the implant relative to a magnet on the prosthesis in accordance with another embodiment of the invention.

FIGS. 4 and 5 illustrate other exemplary embodiments of the present invention wherein the implant body and/or the inner concave surface of the prosthesis have several attractive elements and magnets, respectively. Specifically, a plurality of the attractive elements may be fitted within the anterior portion of the implant in accordance with a desired, spaced array. Likewise, a plurality of magnets 46 may be fitted to the prosthesis. The one or more magnets 46 are specifically positioned to avoid direct axial alignment with the individual attractive elements in the implant body. The magnets, while being offset relative to the position of the attractive elements, still maintain a magnetic attraction with corresponding attractive elements 42 to magnetically couple the prosthesis to the implant body. Magnetic attraction, as used herein, refers to the existence of an attractive force which exists between the magnets 42 and attractive elements 46.

To replace a diseased or traumatized eye using the apparatus of the present invention, a surgical procedure is required wherein a standard enucleation is done, including tagging of the extraocular muscles with absorbable suture. The orbit is sized, using a set of sizing spheres, to determine the size of the implant to be used. An implant is of the proper size when it is the largest implant that can be placed deep into the orbit without creating tension on the overlying tissues and while allowing adequate room for an artificial eye of sufficient thickness. The implant may be placed into the orbit with or without being wrapped in a homologous or autologous material such as preserved sclera, dura, or fascia lata. The surface of the hydroxyapatite material is very rough, and a wrapping material facilitates insertion and placement of the implant deep into the orbit. Additionally, a wrapped implant may be more resistant to exposure caused by abrasion from the surface of the implant on the overlying tissues. If some material is used to wrap the implant, the four rectus muscles should be sutured to the wrapping material.

The rectus muscles should be sutured to each other over the anterior aspect of the implant: lateral to medial and superior to inferior. Tenon's capsule and the conjunctiva should then be closed in separate layers. A temporary wrapping should be made to facilitate placement of the implant deep into the orbit. In one variation, the following technique can be used to place an unwrapped implant. Cut two 13×13 cm squares from the thin, sterile plastic drape used to drape the patient. Overlap two of the edges of the squares by about 1.0 cm and place the implant on the center of the overlap. Wrap the plastic around the implant and gather up the plastic to completely surround the implant. The plastic-wrapped implant can then be easily inserted into the orbit. After placing the implant deep into the orbit, unwrap the plastic and, while holding the implant in place with one finger, gently pull the plastic pieces out from under the implant. After a period of healing of approximately two months, the patient is measured for a cosmetic prosthesis. At this time, magnet positioning on the prosthesis can be determined for proper alignment of the prosthesis with the gaze position of the patient's natural eye, as described above.

In the instance an evisceration is preferable over enucleation, the medically accepted techniques for performing an evisceration are followed. The implant of the present apparatus is then inserted and the orbit is closed. The prosthesis is fitted in the same general manner as is done with the above enucleation procedure.

While the instant invention has been shown and described in what is considered to be preferred and practical embodiments thereof, it is recognized that departures may be made within the spirit and scope of the present invention which, therefore, should not be limited except as set forth within the following claims as interpreted under the doctrine of equivalents.

Now that the invention has been described,

What is claimed is:

1. An ocular replacement system for replacing a natural eye removed from an eye cavity having ocular tissue including muscle tissue and conjunctiva, said ocular replacement system comprising:

a ball-shaped implant body sized and configured for receipt within the eye cavity and having an outer, generally spherical and porous surface that is receptive to ingrowth of the ocular tissue and including an anterior portion having a convex surface configuration defining a portion of said spherical surface of said implant body, said anterior portion being structured and disposed to permit closing of the conjunctiva in covering relation to said anterior portion so that said implant body is completely enclosed within the eye cavity and covered by the ocular tissue;

a prosthesis including an outer convex surface provided with a cosmetically acceptable appearance to resemble the natural eye and an inner concave surface;

magnetic coupling means for providing an attractive force between said anterior portion of said implant body and said inner concave surface of said prosthesis and through the conjunctiva sandwiched between said implant body and said prosthesis to magnetically couple the prosthesis to the implant body so that the prosthesis follows movement of the implant body within the eye cavity; and said magnetic coupling means including:

at least one magnet having an exposed face defining a magnetic pole, said at least one magnet being fitted to said inner concave surface of said prosthesis so that said exposed face is flush with said inner concave surface of said prosthesis;

at least one magnetically attractive element embedded within the anterior portion of said implant body so that an exposed face of said magnetically attractive element is flush with said outer, generally spherical and porous surface; and said at least one magnet and said at least one magnetically attractive element being positioned and disposed in offset, non-axial alignment with each other, with the conjunctiva therebetween, while maintaining a magnetic attraction between said at least one magnet on said prosthesis and said at least one magnetically attractive element on said implant.

2. An ocular replacement system as recited in claim 1 wherein said magnetic coupling means includes a plurality of magnets fitted to said inner concave surface of said prosthesis.

3. An ocular replacement system as recited in claim 1 wherein said magnetic coupling means includes a plurality of said magnetically attractive elements embedded within said anterior portion of said implant body.

4. An ocular replacement system as recited in claim 1 wherein said magnetic coupling means includes a plurality of said magnets fitted to said inner concave surface of said prosthesis and a plurality of said magnetically attractive elements embedded within said anterior portion of said implant body.

5. An ocular replacement system as recited in claim 1 wherein said at least one magnetically attractive element is formed of stainless steel.

6. An ocular replacement system as recited in claim 1 wherein said at least one magnetically attractive element is formed of a metal alloy which is attracted to a magnetic force.

7. An ocular replacement system for replacing a natural eye removed from an eye cavity having ocular tissue including muscle tissue and conjunctiva, said ocular replacement system comprising:
   a ball-shaped implant body sized and configured for receipt within the eye cavity and having an outer, generally spherical and porous surface that is receptive to ingrowth of the ocular tissue and including an anterior portion having a convex surface configuration defining a portion of said spherical surface of said implant body, said anterior portion being structured and disposed to permit closing of the conjunctiva in covering relation to said anterior portion so that said implant body is completely enclosed within the eye cavity and covered by the ocular tissue;
   a prosthesis including an outer convex surface provided with a cosmetically acceptable appearance to resemble the natural eye and an inner concave surface;
   magnetic coupling means for providing an attractive force between said anterior portion of said implant body and said inner concave surface of said prosthesis and through the conjunctiva sandwiched between said implant body and said prosthesis to magnetically couple the prosthesis to the implant body so that the prosthesis follows movement of the implant body within the eye cavity; and
   said magnetic coupling means including:
      at least one magnet having an exposed face defining a magnetic pole, said at least one magnet being fitted to said inner concave surface of said prosthesis so that said exposed face is flush with said inner concave surface of said prosthesis;
      a plurality of magnetically attractive elements embedded within the anterior portion of said implant body so that an exposed face of each of said magnetically attractive elements are flush with said outer, generally spherical and porous surface; and
      said at least one magnet on said prosthesis being positioned and disposed in offset, non-axial alignment relative to said plurality of magnetically attractive elements on said implant body, with the conjunctiva therebetween, while maintaining a magnetic attraction between said at least one magnet and said plurality of magnetically attractive elements.

8. An ocular replacement system as recited in claim 7 wherein said magnetic coupling means includes a plurality of magnets fitted to said inner concave surface of said prosthesis so that said exposed face of each of said plurality of magnets is flush with said inner concave surface of said prosthesis.

9. An ocular replacement system as recited in claim 7 wherein said plurality of magnetically attractive elements are formed of stainless steel.

10. An ocular replacement system as recited in claim 7 wherein said plurality of magnetically attractive elements are formed of a metal alloy which is attracted to a magnetic force.

* * * * *